(12) United States Patent
Broekaart et al.

(10) Patent No.: US 9,733,075 B2
(45) Date of Patent: Aug. 15, 2017

(54) SYSTEM AND METHOD FOR ASSESSING INHOMOGENEOUS DEFORMATIONS IN MULTILAYER PLATES

(75) Inventors: Marcel Broekaart, Theys (FR); Arnaud Castex, Grenoble (FR); Laurent Marinier, Lumbin (FR)

(73) Assignee: Sony Semiconductors Solutions Corporation, Kanagawa (JP)

( * ) Notice: Subject to any disclaimer, the term of this patent is extended or adjusted under 35 U.S.C. 154(b) by 1073 days.

(21) Appl. No.: 13/574,585

(22) PCT Filed: Jan. 24, 2011

(86) PCT No.: PCT/FR2011/050127
§ 371 (c)(1),
(2), (4) Date: Nov. 12, 2012

(87) PCT Pub. No.: WO2011/089368
PCT Pub. Date: Jul. 28, 2011

(65) Prior Publication Data
US 2013/0054154 A1    Feb. 28, 2013

(30) Foreign Application Priority Data

Jan. 25, 2010 (FR) .................................... 10 50468

(51) Int. Cl.
*G01B 5/28*    (2006.01)
*G01B 17/06*    (2006.01)
(Continued)

(52) U.S. Cl.
CPC ............. *G01B 17/06* (2013.01); *G01B 21/32* (2013.01); *G01N 29/0681* (2013.01);
(Continued)

(58) Field of Classification Search
USPC ........................................................ 702/39
See application file for complete search history.

(56) References Cited

U.S. PATENT DOCUMENTS

| | | | |
|---|---|---|---|
| 6,781,702 B2 | 8/2004 | Giannakopoulos et al. | |
| 7,966,135 B2 * | 6/2011 | Rosakis et al. ................. | 702/42 |

(Continued)

FOREIGN PATENT DOCUMENTS

| | | |
|---|---|---|
| CN | 1511247 A | 7/2004 |
| FR | 2 638 846 | 5/1990 |

(Continued)

OTHER PUBLICATIONS

International Preliminary Report on Patentability for International Application No. PCT/FR2011/050127 dated Aug. 7, 2012.

(Continued)

*Primary Examiner* — Paul D Lee
(74) *Attorney, Agent, or Firm* — Sheridan Ross P.C.

(57) ABSTRACT

A method and device for evaluating inhomogeneous deformations in a first wafer bonded by molecular adhesion to a second wafer. This evaluation method includes the steps of making at least one reading of a plurality of measurement points, the reading corresponding to a surface profile of the first wafer along a predefined direction and over a predefined length, computing a second derivative from the measurement points of the surface profile and evaluating a level of inhomogeneous deformations in the first wafer according to the second derivative.

19 Claims, 6 Drawing Sheets

(51) Int. Cl.
*G01B 21/32* (2006.01)
*G01N 29/06* (2006.01)
*G03F 7/20* (2006.01)

(52) U.S. Cl.
CPC .. *G01N 2291/2697* (2013.01); *G03F 7/70616* (2013.01); *G03F 7/70633* (2013.01)

(56) References Cited

U.S. PATENT DOCUMENTS

| | | | |
|---|---|---|---|
| 2001/0028460 A1 | 10/2001 | Maris et al. | |
| 2002/0042664 A1* | 4/2002 | Kikuchi | 700/114 |
| 2003/0106378 A1 | 6/2003 | Giannakopoulos et al. | 73/788 |
| 2005/0031975 A1 | 2/2005 | Reuhman-Huisken et al. | 430/30 |
| 2005/0278126 A1* | 12/2005 | Rosakis et al. | 702/42 |
| 2006/0276977 A1* | 12/2006 | Rosakis et al. | 702/42 |
| 2007/0212856 A1 | 9/2007 | Owen | |
| 2007/0213467 A1 | 9/2007 | Okubo et al. | 525/240 |
| 2007/0220458 A1* | 9/2007 | Zhou et al. | 716/5 |
| 2009/0095086 A1 | 4/2009 | Kessler et al. | 73/606 |
| 2009/0217767 A1* | 9/2009 | Scherschlicht | 73/779 |
| 2009/0280595 A1 | 11/2009 | Broekaart et al. | |
| 2011/0144943 A1* | 6/2011 | Veeraraghavan et al. | 702/167 |

FOREIGN PATENT DOCUMENTS

| | | |
|---|---|---|
| JP | 11-287630 A | 10/1999 |
| TW | 201005812 A | 2/2010 |
| WO | WO 2007/103566 A2 | 9/2007 |
| WO | WO 2009/135800 A2 | 11/2009 |

OTHER PUBLICATIONS

International Search Report for International Application No. PCT/FR2011/050127 dated Apr. 18, 2011, 3 pages.
International Written Opinion for International Application No. PCT/FR2011/050127 dated Apr. 18, 2011, 6 pages.
Taiwanese Office Action and Search Report for Taiwan Application No. 100106950 dated May 11, 2015, 9 pages.
International Search Report, PCT/FR2001/050127, mailed Apr. 18, 2011.

* cited by examiner

SYSTEM AND METHOD FOR ASSESSING INHOMOGENEOUS DEFORMATIONS IN MULTILAYER PLATES

This application is a 371 filing of International Patent Application PCT/FR 2011/050127 filed Jan. 24, 2011.

BACKGROUND OF THE INVENTION

The present invention relates to the field of the production of multilayer semiconductor wafers or substrates produced by transfer of at least one layer formed from an initial substrate onto a final substrate, the layer transferred corresponding to a portion of the initial substrate. The layer transferred may further comprise all or part of a component or of a plurality of microcomponents.

The present invention concerns the problem of the heterogeneous deformations that occur in a layer bonded by molecular adhesion to a substrate, and to be more precise on the transfer of such a layer from an initial substrate called the "donor substrate" to a final substrate called the "receiver substrate". Such deformations have notably been observed in the case of the technology of three-dimensional integration of components (3D-integration) which necessitates the transfer of one or more layers of microcomponents onto a final support substrate but also in the case of transfer of circuits or in the production of back-lit imaging devices. Because in particular of the very small size and the large number of microcomponents generally present on the layers transferred, each of them must be positioned on the final substrate with great accuracy in order to comply with a very strict alignment with the underlying layer. Moreover, it may be necessary to carry out treatments on the layer after its transfer, for example to form other microcomponents, to uncover microcomponents on the surface, to make interconnections, etc.

However, the Applicant has noticed that after such a transfer there exist situations in which it is very difficult or even impossible to form additional microcomponents in alignment with the microcomponents formed before the transfer.

This phenomenon of misalignment is described with reference to FIGS. 1A to 1E which show one embodiment of a three-dimensional structure comprising the transfer onto a final substrate of a layer of microcomponents formed on an initial substrate and the formation of an additional layer of microcomponents on the exposed face of the initial substrate after bonding.

Figure 1A:
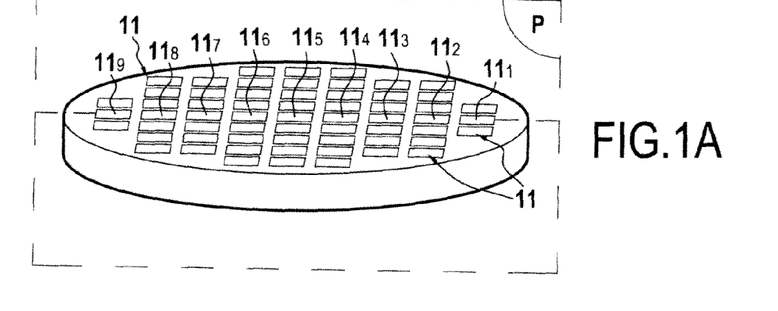
FIGS. 1A to 1E are diagrammatic views showing the production of a prior art three-dimensional structure.
Figure 1B:
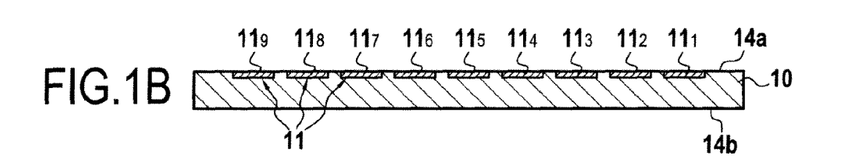

FIGS. 1A and 1B show an initial substrate 10 on which is formed a first series of microcomponents 11. The microcomponents 11 are formed by photolithography by means of a mask enabling definition of the areas of formation of patterns corresponding to the microcomponents 11 to be produced.

Figure 1C:
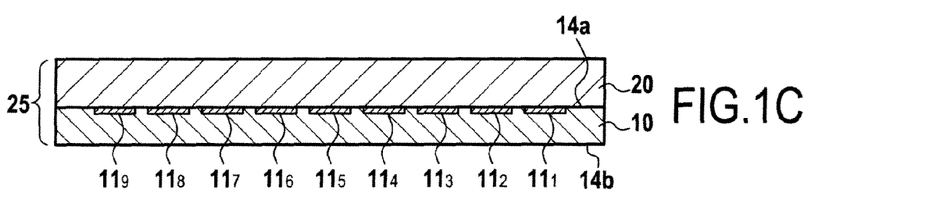
Figure 1D:
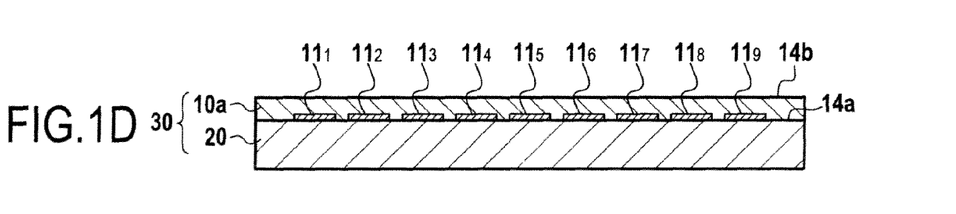

As shown in FIG. 1C, the face of the initial substrate 10 comprising the microcomponents 11 is then brought into intimate contact with a face of a final substrate 20, thus forming the composite structure 25. The bonding between the initial substrate 10 and the final substrate 20 is effected by molecular adhesion. There is thus obtained a buried layer of microcomponents 11 at the bonding interface between the substrates 10 and 20. After bonding, and as shown in FIG. 1D, the initial substrate 10 is thinned in order to remove a portion of material present over the layer of microcomponents 11. A thinned composite structure 30 is then obtained formed of the final substrate 20 and a layer 10a corresponding to the remaining portion of the initial substrate 10.

Figure 1E:
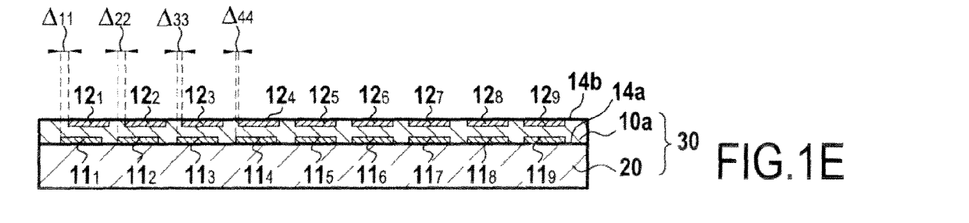

As shown in FIG. 1E, the next step in the production of the three-dimensional structure consists in forming a second layer of microcomponents 12 at the level of the exposed surface of the thinned initial substrate 10, or in carrying out complementary technological steps on this exposed surface, in alignment with the components included in the layer 10a (contacts, interconnections, etc.). For simplicity, in the remainder of this text the term "microcomponents" refers to devices or any other patterns resulting from technology steps effected on or in the layers and the positioning of which must be controlled accurately. It may thus be a question of active or passive components, contacts or interconnections.

Thus, in order to form the microcomponents 12 in alignment with the buried microcomponents 11, a photolithographic mask is used similar to that used to form the microcomponents 11. Here similar masks means masks that were designed to be used in association during a fabrication process.

The layers transferred, such as the layer 10a, typically comprise marks (or markers) both at the level of the microcomponents and at the level of the slice forming the layer that are notably used by positioning and alignment tools during technological treatment steps such as those executed for the purposes of photolithography.

However, even if positioning tools are used, offsets arise between some of the microcomponents 11 and 12, such as the offsets $\Delta 11$, $\Delta 22$, $\Delta 33$, $\Delta 44$ indicated in FIG. 1E (respectively corresponding to the offsets observed between the pairs of microcomponents 111/121, 112/122, 113/123 and 114/124).

These offsets are not the result of basic transformations (translation, rotation or combinations thereof) that could originate in inaccurate assembly of the substrates. These offsets result from heterogeneous deformations that occur in the layer coming from the initial substrate when it is assembled with the final substrate. These deformations lead to local and non-uniform movements at the level of some microcomponents 11. Also, some of the microcomponents 12 formed on the exposed surface 14b of the substrate after transfer feature variations of position with these microcomponents 11 that may be of the order of several hundred nanometres or even one micron.

The phenomenon of so-called "overlay" or misalignment between the two layers of microcomponents 11 and 12 may be the source of short circuits, distortions in the stack or connection faults between the microcomponents of the two layers. Thus if the microcomponents transferred are imagers formed of pixels and the post-transfer processing steps are aimed at forming colour filters on each of these pixels, there has been observed a loss of the colorization function for some of these pixels.

This misalignment phenomenon thus leads to a reduction in the quality and the value of the multilayer semiconductor wafers produced. The impact of this phenomenon becomes more and more critical because of the ever increasing requirements in respect of miniaturization of microcomponents and their integration density in each layer.

The method routinely used nowadays to determine if significant heterogeneous deformations are present in a multilayer wafer consists in determining the positioning of a number of microcomponents by carrying out optically measurements of position at the level of markers formed on or in the vicinity of those microcomponents (verniers, etc.).

However, it is possible to proceed to these positioning tests only after thinning the initial substrate and carrying out complementary technological steps on the exposed surface 14b of the initial substrate 10.

Moreover, if alignment defects are detected in the initial substrate after it is thinned, they cannot be corrected. In this case, the thinned initial substrate cannot be recycled. In the final analysis, if positioning tests reveal in a thinned composite structure misalignments that are unacceptable in terms of reliability and/or performance, the final substrate is lost, which significantly increases the cost of production of multilayer wafers.

A technique for determination of misalignments in a semiconductor wafer is moreover described in the patent document WO 2007/103566 A2. To be more precise, this technique aims to evaluate misalignments liable to occur in a wafer during a photolithography step, these misalignments resulting from mechanical stresses generated in the wafer.

In practise, this technique consists in carrying out curvature measurements on one face of a layer produced by deposition on a substrate. From curvature data obtained at different points of the layer, the internal mechanical stresses of this layer relative to the substrate are determined. Knowing these stresses, it is possible to evaluate the "movements" of this layer relative to the substrate. The evaluation of these movements before or during a photolithography step notably makes it possible to determine how to compensate or correct the photolithography parameters in such a manner as to minimize the misalignments.

However, this technique concerns only the evaluation of deformations generated over the whole of a layer produced by deposition on a substrate (or possibly by ion implantation, annealing or etching). These so-called homogeneous deformations are in fact the result of a mechanical equilibrium obtained over the whole of the layer deposited on the substrate. This type of deformation exhibits a behaviour that is now relatively predictable thanks to the use of models taking into account in particular the laws of mechanics and the thicknesses in play (cf. equation 5 on page 5 of the document WO 2007/103566 A2).

The technique described in the document WO 2007/103566 A2 is, not designed to evaluate heterogeneous deformation resulting from bonding of two wafers, however, and in particular bonding of molecular adhesion type the mechanisms whereof are still very badly understood at present.

The Applicant has noticed that the behaviour of the heterogeneous deformations resulting from bonding by molecular adhesion is random and in any event very different from the classic homogeneous deformations. At this writing, no model enables reliable evaluation of the level of heterogeneous deformations generated in a layer bonded by molecular adhesion to a substrate. There therefore exists a requirement to evaluate in a simple and effective manner the level of heterogeneous deformations in multilayer structures produced by bonding by molecular adhesion, at an earlier stage of their fabrication.

OBJECT AND SUMMARY OF THE INVENTION

One of the objects of the invention is to propose a solution enabling a response to be given to the requirement as formulated hereinabove. To this end, the present invention proposes a method for evaluation of heterogeneous deformations in a first wafer, the first wafer being bonded by molecular adhesion to a second wafer, the evaluation method comprising:

a step of surveying a plurality of measurement points, each of the measurement points being locally representative of the level of the exposed surface of the first wafer;

a step of determination of at least one surface profile of the first wafer passing through a plurality of measurement points;

a step of processing the surface profile of the first wafer to determine therefrom a magnitude characteristic of the processed surface profile; and a step of evaluation of a level of heterogeneous deformations in said first wafer as a function of said characteristic magnitude.

Thanks to the evaluation method of the invention it is possible to evaluate the level of heterogeneous deformations in an initial substrate immediately after it is bonded to a final substrate.

Based on the evaluation of a level of heterogeneous deformation, it is possible to estimate the offsets that have occurred between the buried surface and the exposed surface of the initial substrate. More particularly, the method of the invention enables estimation of the level of misalignments that would be likely to come about if microcomponents were to be fabricated on the exposed surface of the initial substrate.

Thus a simple and effective evaluation of the heterogeneous deformations is possible before proceeding to the thinning of the initial substrate. The evaluation method of the invention does not necessitate the presence of microcomponents on the exposed surface of the initial substrate or even the presence of microcomponents buried in the initial substrate in such a manner as to be observable optically through a relatively small thickness of the remaining initial substrate. The evaluation of a level of heterogeneous deformations may thus be carried out very far upstream in the fabrication process of a three-dimensional structure.

The evaluation method of the invention is preferably carried out just after bonding of the initial substrate to the final substrate by molecular adhesion. This avoids carrying out additional technology steps (thinning, production of microcomponents, etc.) that could prove of no utility and costly if excessive misalignments were detected afterwards in the initial substrate.

When excessive heterogeneous deformations are detected in an initial substrate after bonding, it is then possible to detach the initial substrate from the final substrate and to try bonding by molecular adhesion again. The evaluation method of the invention thus enables reuse (i.e. recycling) of an initial substrate if the bonding has led to heterogeneous deformation.

In a first particular embodiment, the surface profile is determined by measurement points disposed along a diameter of the first wafer. This situation applies of course when the first wafer has a substantially cylindrical shape.

It is thus possible to log measurement points on different diameters of the first wafer in order to obtain data representative of the heterogeneous deformations over the whole of the first wafer.

In this first embodiment, the characteristic magnitude is preferably the second derivative of the surface profile.

Moreover, the evaluation step of the evaluation method may comprise at least one of the following tests:

a first test to determine if the second derivative has at least one change of sign; and a second test to determine if the second derivative has at least one absolute value greater than a predetermined value.

Each of these two tests enables simple and effective evaluation of a level of heterogeneous deformations in an initial substrate after bonding by molecular adhesion to a final substrate.

In one embodiment of the invention, only one of the two tests described above is carried out.

Alternatively, both tests are carried out to evaluate a level of heterogeneous deformations in the first wafer.

In a second embodiment, the surface profile is determined by measurement points disposed along a circle the centre of which coincides with the centre of said first wafer.

In one particular embodiment, the evaluation method comprises carrying out the following steps:
  determination of a plurality of surface profiles of the first wafer,
  for each surface profile of the plurality of surface profiles, carrying out of a processing step for determining therefrom a magnitude characteristic of the processed profile, wherein, during the evaluation step, the level of heterogeneous deformations is determined as a function of said characteristic magnitudes so determined.

Alternatively, a plurality of logs of measurement points may be produced, the logs being spaced from each other and produced in the same direction. In this way, all the logs of measurement points produced are parallel to each other in a first direction. There may in particular be envisaged the situation in which the logs are uniformly spaced from each other and oriented according to the same first direction.

Moreover, and still in the context of this alternative, it is possible to produce a plurality of additional logs in which the measurement points of each of the logs are in the same second direction, this second direction being different from the first direction mentioned above. For example logging of measurement points may be carried out in accordance with a grid formed by lines parallel to the first and second directions. This grid could be uniform and the first and second directions could be chosen to be perpendicular.

Moreover, the measurement points of each log may be measured with a measurement step, the measurement step being determined as a function of a dimension of at least one pattern of the first wafer.

In one particular embodiment, the measurement step may substantially correspond to half a dimension of a pattern of said first wafer. In one particular case, a pattern has a rectangular shape on the exposed surface of the initial substrate, the measurement step substantially corresponding to half of one side of this pattern.

The choice of an appropriate measurement step, and this as a function of a dimension of a pattern of the first wafer, is advantageous in that it enables no account to be taken of any infinitesimally small variations in the level of the exposed surface of the first wafer, these variations causing very localized changes of sign of the second derivative of the corresponding surface profile.

Moreover, the logging of a plurality of measurement points may be carried out by acoustic microscopy.

The present invention also concerns a method of selection of at least one structure comprising a first wafer bonded by molecular adhesion to a second wafer, the selection method comprising:
  a step of evaluation of the heterogeneous deformations in the first wafer of each structure by the evaluation method as described above; and
  a step of selection of one or more structures on the basis of the characteristic magnitudes determined for each structure evaluated.

Accordingly, if the first test and the second test are carried out during the evaluation step, for example, a structure is selected only if these two tests are negative.

The selection method of the invention enables retention, from a batch comprising a plurality of multilayer structures, of the satisfactory structures, i.e. those that have an acceptable level of heterogeneous deformations, and elimination of the structures having an unacceptable level of non-homogenous deformations.

The present invention further concerns a device for evaluation of heterogeneous deformations in a first wafer, the first wafer being bonded by molecular adhesion to a second wafer, the evaluation device comprising:
  measuring means for surveying a plurality of measurement points, each of said measurement points being locally representative of the level of the exposed surface of the first wafer;
  calculation means for determining at least one surface profile of the first wafer passing through a plurality of the measurement points and for determination of a magnitude characteristic thereof; and
  evaluation means for evaluating a level of heterogeneous deformations in the first wafer as a function of the characteristic magnitude.

It will be noted that the advantages stated and comments made with reference to the various embodiments of the evaluation method and the selection method of the invention apply in analogous manner to the various embodiments of the evaluation device and the selection device of the invention.

In one particular embodiment, the characteristic magnitude is the second derivative of the surface profile.

In this embodiment, the evaluation means may be configured to execute at least one of the following tests:
  a first test for determining if the second derivative has at least one change of sign; and
  a second test for determining if the second derivative has at least one absolute value greater than a predetermined value.

The measuring means may be configured so that the measurement points of each log are measured along a diameter of the first wafer.

Alternatively, the measuring means are configured to produce a plurality of logs of measurement points, the logs being spaced from each other and produced in the same direction.

The measuring means may further be configured so that the measurement points of each log are measured with a measurement step, the measurement step being determined as a function of a dimension of at least one pattern of the first wafer.

In one particular embodiment, the measurement step substantially corresponds to half a dimension of a pattern of the first wafer.

Moreover, the measuring means of the invention may comprise an acoustic microscope.

BRIEF DESCRIPTION OF THE DRAWINGS

Other features and advantages of the invention will emerge from the following description of particular embodiments of the invention, provided by way of example, given with reference to the appended drawings, in which.

DETAILED DESCRIPTION OF ONE EMBODIMENT

The present invention proposes a solution enabling evaluation of a level of heterogeneous deformations in a first wafer corresponding to an initial substrate bonded by molecular adhesion to a second wafer corresponding to a final substrate.

Figure 2:
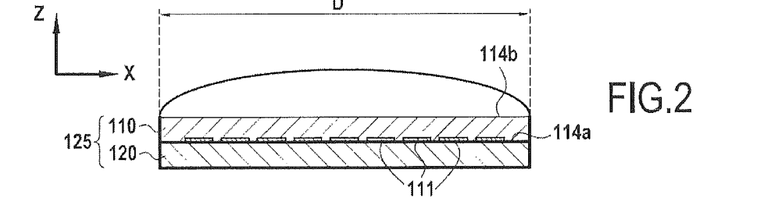
FIG. 2 is a perspective half-section of a composite structure comprising a first wafer bonded to a second wafer.

Considered here is the case of the composite structure 125 as shown in FIG. 2. In this example, the composite structure 125 is formed by bonding by molecular adhesion a first wafer 110 having microcomponents 111 on its bonding surface 114a to a second wafer 120 so as to bury the microcomponents 111 at the level of the bonding interface.

In the examples described here, the wafers used to form the composite structure 125 have a diameter of 300 mm. It will nevertheless be understood that the invention applies to other wafer sizes and/or shapes.

There are described with reference to FIG. 3 the main steps (steps E1 to E3) of the evaluation method of one embodiment of the invention, this method enabling evaluation of a level of heterogeneous deformations in the composite structure 125 shown in FIG. 2.

The Applicant has found, surprisingly, that it is possible to obtain information on the heterogeneous deformations in the first wafer 110 by studying the reliefs on the exposed surface 114b of the first wafer 110.

Thus there is first carried out a step E1 of logging a plurality of measurement points, each measurement point being locally representative of the level of the exposed surface of the wafer 110. Each logging effected thus corresponds to a surface profile of the first wafer 110 in a particular direction or along a particular curve and over a particular length.

Thus here surface profile means a profile representative of the relief (or level) of a surface in a particular direction or a particular curve and over a particular length.

In the present case, each log of measurement points is locally representative of the level or relief of the exposed surface 114b of the first wafer 110 vis-à-vis an axis Z perpendicular to said exposed surface 114b.

The or each log of measurement points is typically effected by means of mechanical or optical profilometry equipment (by interferometry, for example). The logs are preferably produced using an acoustic microscopy technique, this technique enabling advantageous reduction in the measurement time of each log.

Figures 3, 7:
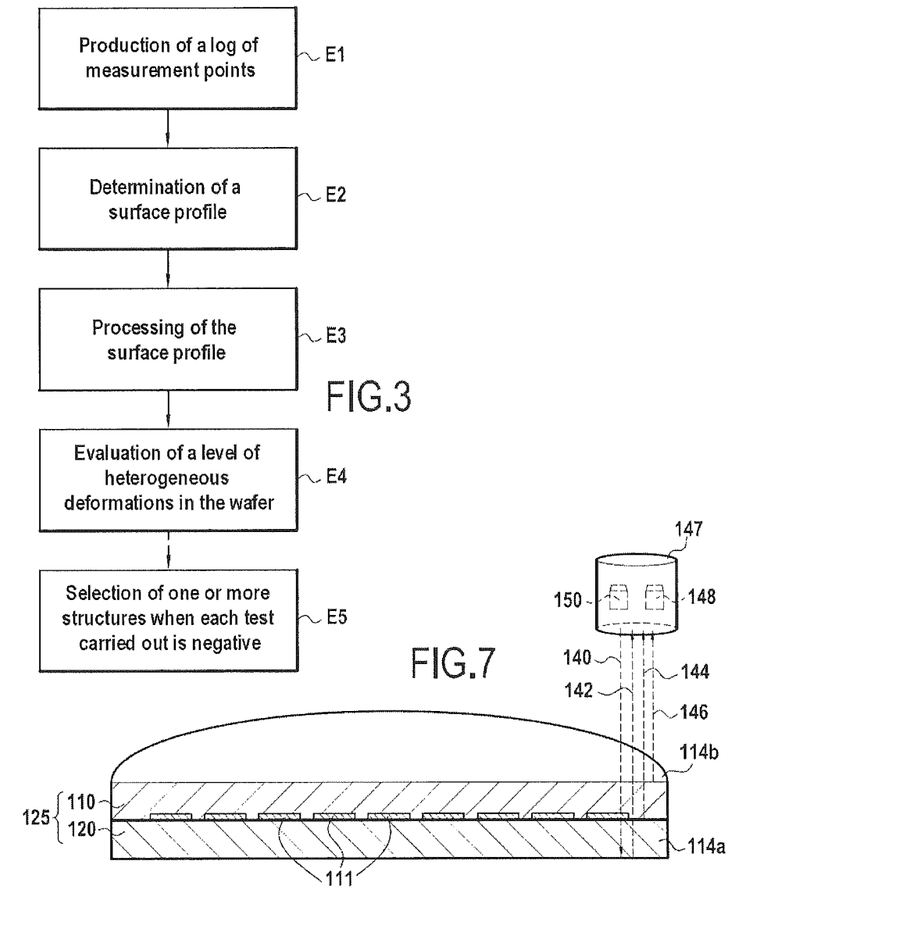
FIG. 3 represents, in flowchart form, the main steps of an evaluation method and a selection method conforming to one particular embodiment of the invention.
FIG. 7 represents diagrammatically an example of an acoustic microscopy technique for measuring a surface profile.

FIG. 7 represents diagrammatically an example of an acoustic microscopy technique enabling measurement of a profile of the exposed surface 114b of the first wafer 110.

A probe 147 comprises a source 148 configured to emit an incident acoustic wave 140 in the direction of the composite structure 125. This acoustic wave propagates in the first wafer 110 and then in the second wafer 120, thus encountering three successive interfaces, namely the exposed surface 114b of the first wafer 110, then the buried surface 114a of the first wafer 110, and finally the rear face of the second wafer 120. The acoustic wave 140 is partially reflected at each interface, each time producing an echo that is sent back to the acoustic sensor 150 of the probe 147. There is thus detected by means of the acoustic sensor 150 the reception of the echoes 142, 144 and 146 respectively resulting from the reflection of the acoustic wave 142 at the rear face of the second wafer 120, at the buried surface 114a and at the exposed surface 114b.

It is then possible to determine the distance between the wafer 147 and the exposed surface 114b of the first wafer 110 from the time necessary for the echo 146 to reach the probe 147. Alternatively, the thickness of the first wafer may be measured at a given position from the time shift between reception of the echo 146 and reception of the echo 144.

By moving the probe in front of the composite structure 125, it is thus possible to produce a log of measurement points corresponding to a profile of the exposed surface 114b of the first wafer 110.

In the example described here the measurement points are logged along a diameter D of the first wafer 110. In a second example, the measurement points are logged along a circle (or a circular arc) the centre of which coincides with the centre of the wafer 110 and the radius of which is less than the radius of the wafer.

However, it is possible to carry out more than one logging of measurement points in any direction and/or over any distance. Moreover, the direction and the length of each log may be chosen as a function notably of the constraints and requirements of a given situation (the technology concerned, the required level of reliability, the equipment used, etc.). To continue the second example from above, the log may consist in a series of concentric circles the centres of which coincide with the centre of the wafer 110 and the radii of which are chosen so as to distribute the measurement points over the surface of the wafer.

There is then effected a step E2 of determination of at least one surface profile of the wafer 110, each profile passing through a plurality of measurement points of a log produced in the step E1. A surface profile may thus correspond to some or all of the measurement points of a log produced in the step E1. If a plurality of measurement loggings were produced in the step E1, a measurement profile is determined for each of them in the step E2.

Once the step E2 has been effected, processing is carried out (step E3) for each surface profile obtained in the step E2 in order to deduce therefrom a corresponding characteristic magnitude. As explained in more detail hereinafter, this characteristic magnitude may be of a different kind.

To be more precise, the Applicant has determined that different treatments based on the surface profile determined in the step E2 enable information to be obtained representative of the level of heterogeneous deformations present in the wafer 110.

In a first embodiment of the invention, during the step E3, a second derivative is calculated from measurement points obtained along the diameter D of the wafer 110. The second derivative calculated in this way provides information on the variations of the slope of the surface profile along that diameter.

The Applicant has noted, surprisingly, that the second derivative of a surface profile provides information representative of the level of heterogeneous deformations existing in the first wafer 110 bonded by molecular adhesion to the second wafer 120. In a second embodiment of the invention, there is determined during the processing step E3 the spread of a surface profile determined in the step E2, that surface profile corresponding to a circular log. The Applicant has observed, surprisingly, that the spread (as measured by a standard deviation or the difference between the maximum and minimum values) of a surface profile corresponding to a circular log also provides information representative of the level of heterogeneous deformations existing in the first wafer 110 bonded by molecular adhesion to the second wafer 120.

There is then carried out (step E4) an evaluation of the levels of heterogeneous deformations of the first wafer 110 as a function of the characteristic magnitude obtained in the step E3. This evaluation enables estimation of the misalignments that are liable to occur later in the fabrication of a heterostructure such as that described with reference to FIG. 1E.

Referring to the case of FIG. 1, for example, the invention enables estimation of the level of alignment faults Δ11, Δ22, Δ33 and Δ44 that would be obtained by fabricating the microcomponents 12 with a photolithography mask similar to that used to fabricate the microcomponents 11.

To this end, the Applicant has found that there are various ways to exploit the characteristic magnitude (i.e. the second derivative or the spread) of a surface profile to evaluate a level of heterogeneous deformations in a wafer.

Figure 4A:
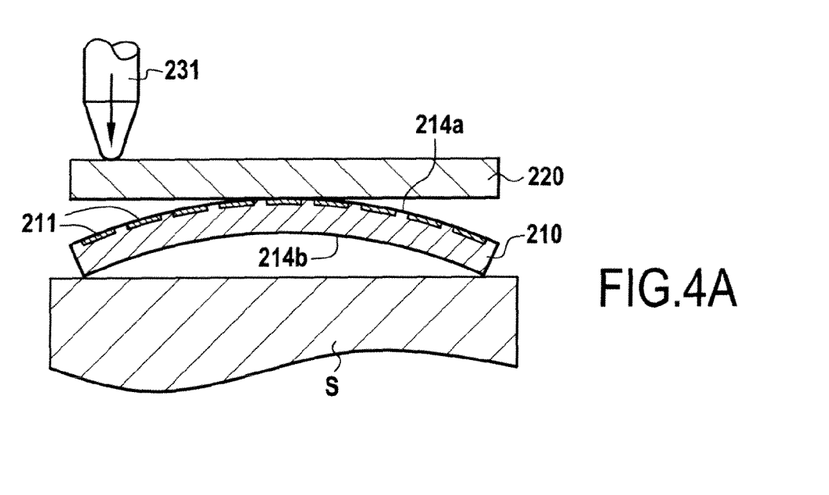
FIGS. 4A, 4B, 4C and 4D respectively represent a diagrammatic view of a first example of bonding a first wafer to a second wafer, the curve of a surface profile corresponding to this first example, the curve of the corresponding second derivative along a particular diameter, and a curve representative of the misalignments present in the first wafer along a particular radius.
Figure 5A:
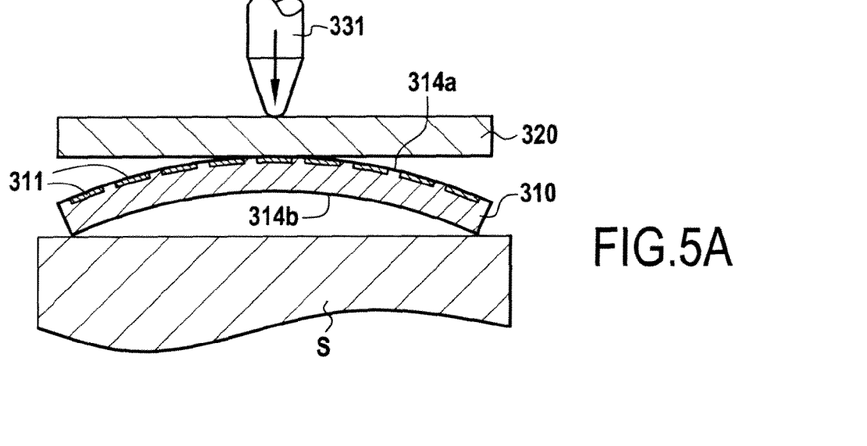
FIGS. 5A, 5B, 5C and 5D respectively represent a diagrammatic view of a second example of bonding a first wafer to a second wafer, the curve of a surface profile corresponding to this second example, the curve of the corresponding second derivative along a particular diameter, and a curve representative of the misalignments present in the first wafer along a particular radius.
Figure 6A:
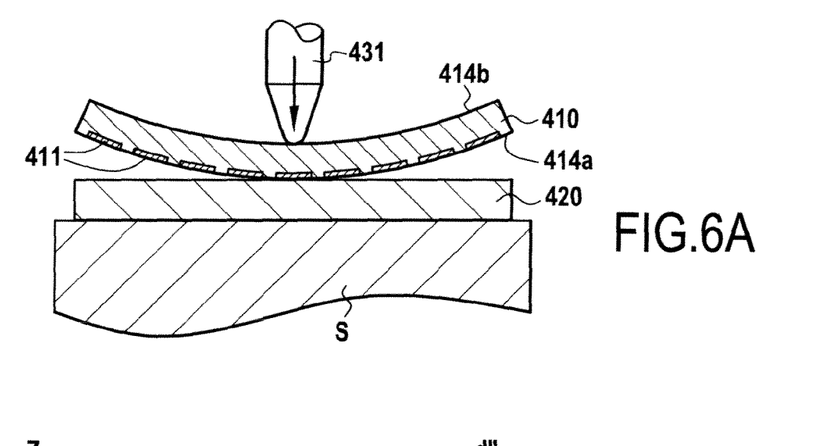
FIGS. 6A, 6B, 6C and 6D respectively represent a diagrammatic view of a third example of bonding a first wafer to a second wafer, the curve of a surface profile corresponding to this third example, the curve of the corresponding second derivative along a particular diameter, and a curve representative of the misalignments present in the first wafer along a particular radius.

Examples of using a second derivative of a surface profile enabling evaluation of a level of heterogeneous deformations (first embodiment) are described first with reference to the examples of FIGS. 4A, 5A and 6A.

In all the examples considered here, the first wafers 210, 310 and 410 have a slightly concave shape before they are bonded to the second wafers 220, 320 and 420, respectively. For clarity, the curvature of the first wafers 210, 310 and 410 has been intentionally exaggerated in FIGS. 4A, 5A and 6A, respectively. Moreover, in each of these examples, microcomponents (211, 311 and 411) are present on the surface (214a, 314a and 414a) of the first wafer (210, 310 and 410).

In the first and second cases shown in FIGS. 4A and 5A, respectively, the first wafers 210 and 310 are placed on a support S (commonly known as a chuck) and have a concave shape on that support. The curvature of the first wafers 210 and 310 is directed away from the support S so that the surfaces 214a and 314a comprising the microcomponents 211 and 311 are exposed.

The second wafers 220 and 320 are then placed on the surfaces 214a and 314a of the first wafers 210 and 310, respectively, in order to proceed to bonding.

A contact force is applied over a region (or at a point) on the second wafers 220 and 320 by means of an applicator tool (respectively denoted 231 and 331). The contact force generated by the applicator tools 231 and 331 in each case enables initiation of a bonding wave between the first and second wafers. The first wafers 210 and 310 are thus bonded by molecular adhesion to the second wafers 220 and 320, respectively. In each case, the microcomponents are then buried at the bonding interface between the first and second wafers.

In the first case (FIG. 4A), the contact force is applied at the peripheral edge of the second wafer 220. In the second case (FIG. 5A), on the other hand, the contact force is applied at the centre of the second wafer 320.

The third case shown in FIG. 6A differs from the first and second cases in that the second wafer 420 is positioned directly on the support S. The first wafer 410 is then placed on the second wafer 420, the face 414a of the first wafer 410 comprising the microcomponents 411 being directed toward the second wafer 420.

A contact force is then applied at the centre of the first wafer 410 by means of an applicator tool 431 in order to initiate the propagation of a bonding wave between the first wafer 410 and the second wafer 420.

In the three cases considered here a composite structure is therefore obtained comprising a first wafer bonded by molecular adhesion to a second wafer (as shown in FIG. 2). Note that, in the examples described here, a contact force of 3.7 N is applied for 6 seconds to initiate the bonding wave.

Heterogeneous deformations are then liable to occur in the first wafers 210, 310 and 410 following their assembly with the second wafers 220, 320 and 420, respectively.

It will further be noted that, in the three cases represented in FIGS. 4A, 5A and 6A, the second wafers 220, 320 and 420 are of plane shape. However, the second wafer may in each case have a non-plane shape, for example a concave shape similar to or different from the first wafer with which it is assembled.

Once bonding by molecular adhesion has been effected in each of the three cases considered above, there follows the evaluation of the levels of heterogeneous deformations in the first wafer of each of the composite structures obtained.

Initially, a log of a plurality of measurement points on the exposed surface of the first wafer of each of the composite structures is produced (step E1).

In the cases describes here, the measurement points are logged along a particular diameter D of the first wafers 210, 310 and 410 by acoustic microscopy.

Each measurement point corresponds to a height Z of the exposed surface of the first wafer relative to a predetermined reference height, each height being associated with a given position on the surface of the first wafer. In the examples described here, the position of each measurement point is defined by a position X along the diameter D concerned.

Alternatively, each measurement point may equally be associated with a pair of coordinates (X,Y) corresponding to a position in two dimensions on the exposed surface of the first wafer.

Moreover in each of the examples described here, the step E1 of producing logs of measurement points further comprises the production of a curve representative of the surface profile obtained in this way.

On the other hand, the subsequent steps of the method of the invention may be carried out without it being necessary to produce such curves.

Figure 4B:
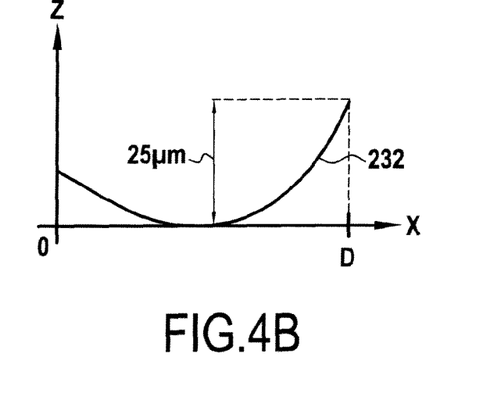
Figure 5B:
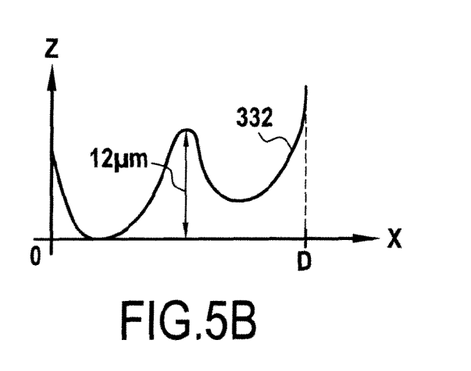
Figure 6B:
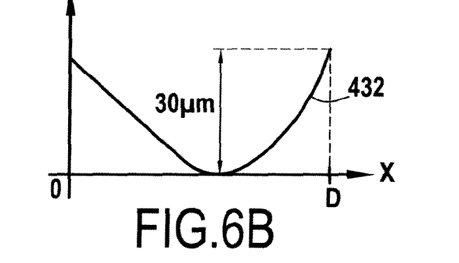

FIGS. 4B, 5B and 6B represent the surface profiles 232, 332 and 432, respectively, observed for the three cases considered.

Figure 4C:
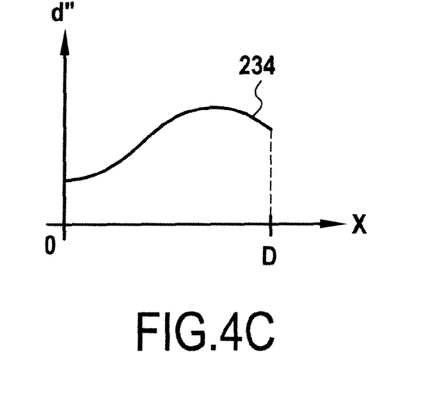

The study of the surface profiles 232, 332 and 432 has shown height variations of the order of 25 μm in the FIG. 4A example, 12 μm in the FIG. 4B example, and 30 μm in the FIG. 4C example.

There follows the step E2 of calculating the second derivatives from the surface profiles obtained in the step E1.

As indicated above, the production of the curves 232, 332 and 432 is not necessary, as each second derivative can be calculated directly from measurement points of the corresponding log.

Figure 5C:
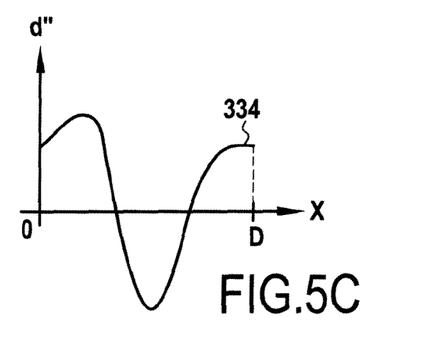
Figure 6C:
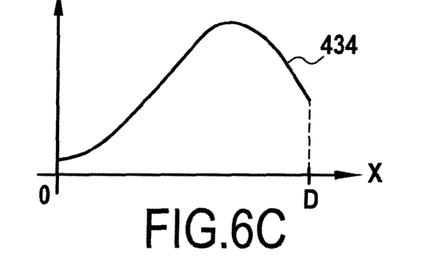

In each of the examples considered here, the calculation step E2 further comprises the production of a curve representative of the second derivative obtained in this way. The curves 234, 334 and 434 correspond to the second derivatives of the three surface profiles 232, 332 and 432, respectively.

It is nevertheless possible to evaluate a level of heterogeneous deformations without producing any graphical representation of the second derivatives. It is possible to limit the process to the calculation and exploitation of the values of each second derivative.

The second derivatives calculated in the step E2 enable evaluation of a level of heterogeneous deformations in the first wafer for the three cases considered (evaluation step E3).

The Applicant has noticed that the second derivative of a surface profile is representative of the deformations on the surface of the first wafer and that by studying these surface deformations it is possible to evaluate a level of heterogeneous deformations in the first wafer.

It has for example been found that the presence of at least one change of direction of curvature in the same surface profile demonstrates the existence of large heterogeneous deformations in the first wafer.

In one particular embodiment of the invention, there is therefore effected a first test consisting in determining if a second derivative of a surface profile includes at least one change of sign. If this first test is positive, there is deduced from this that large heterogeneous deformations exist in the first wafer considered.

The efficacy of this first test has been verified experimentally by evaluating the level of heterogeneous deformations in the three composite structures tested using the acoustic microscopy technique described above with reference to FIG. 7.

To be more precise, in the first case (FIG. 4A), there were observed on the surface 214b of the first wafer 210 misalignments for the most part less than 100 nm, and even less than 50 nm at the centre of the wafer. Only approximately 15% of the surface 214b have misalignments greater than 150 nm. These large misalignments are distributed at the peripheral edge of the wafer, in particular in the region close to the point of contact of the applicator tool 231.

In the second case (FIG. 5A), there were observed misalignments greater than 150 nm over approximately 50% of the exposed surface 314b of the first wafer 310. These large misalignments are distributed for the most part at the centre and at the peripheral edges of the surface 314b. The remaining 50% of the surface 314b has for the most part misalignments from 50 nm to 150 nm.

In the third case (FIG. 6A) it was observed that approximately 75% of the surface 14b of the first wafer 10 have misalignments less than 100 nm. Greater misalignments, generally from 100 nm to 150 nm, are present at the centre of the first wafer 410.

Figure 4D:
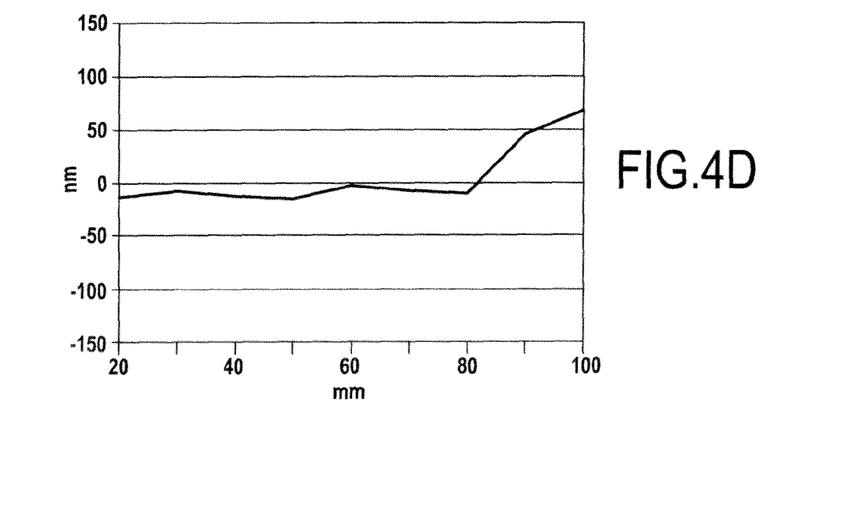
Figure 5D:
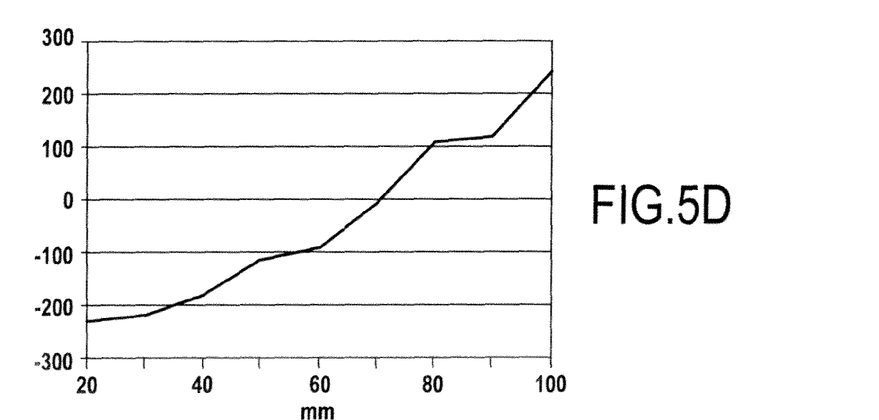
Figure 6D:
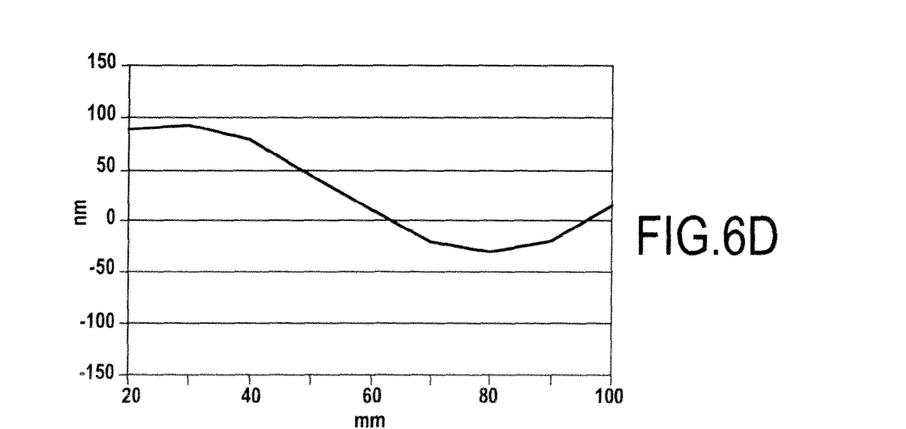

FIGS. 4D, 5D and 6D represent in the form of curves the misalignments measured along a particular radius of each of the first wafers 210, 310 and 410, respectively.

In these three cases, the misalignments present on the first wafer were measured using a standard measurement process, as described with reference to FIGS. 1A to 1E: the first wafer is thinned after bonding, after which there are measured the misalignments present between the microcomponents buried at the bonding interface between the two wafers and the microcomponents fabricated on the exposed surface of the thinned first wafer.

The abscissa axis in FIGS. 4D, 5D and 6D represents the distance (in mm) relative to the centre of the first wafer.

In the final analysis, the samples tested for the second case (FIG. 5A) are those that have the highest levels of non-homogenous deformations. This is confirmed by the fact that only the second derivative 334 of the surface profile 332 includes at least one change of sign. To be more specific, it has been found that the second derivative 334 includes two changes of sign, which reveals large variations of slope at the surface of the first wafer 310.

Conversely, for the samples tested for the first and third cases, the second derivatives include no change of sign, which indicates that these cases lead to lower levels of heterogeneous deformations than the second case.

It will be noted that the number of changes of sign detected in the second derivative of the same surface log may equally provide information on the level of heterogeneous deformations existing within the first wafer.

Moreover, the Applicant has observed that a surface profile having strong slope variations and therefore high second derivative values could equally correspond to large heterogeneous deformations within the first wafer.

Accordingly, in a variant of this first embodiment of the invention, the evaluation of a level of heterogeneous deformations in the first wafer is carried out as a function of the values of the second derivative obtained in the step E2.

For example, there is effected during the evaluation step E3 a second test consisting in determining if a second derivative of a surface profile includes at least one value greater than a predetermined threshold value. If this second test is positive, that means that large heterogeneous deformations are present in the first wafer.

Note that this predetermined value may notably be chosen as a function of the constraints and requirements of the situation concerned (technology concerned, required level of reliability, equipment used, etc.).

The tests described hereinabove are nevertheless given by way of example so that other methods of exploiting the second derivative of a surface profile may be used according to the situation. For example, the number of times a second derivative of a surface profile overshoots a predetermined value may be taken into account, for example, and so on.

Evaluating a level of heterogeneous deformations may also be envisaged that combines different tests relating to the second derivative of surface profiles, for example by cumulation of the first and second tests described above.

There is described now an embodiment in which the characteristic magnitude obtained in the processing step E3 corresponds to a spread of a surface profile (second embodiment), this profile determined in the step E2 corresponding to a log of measurement points of circular shape.

Figure 8A:
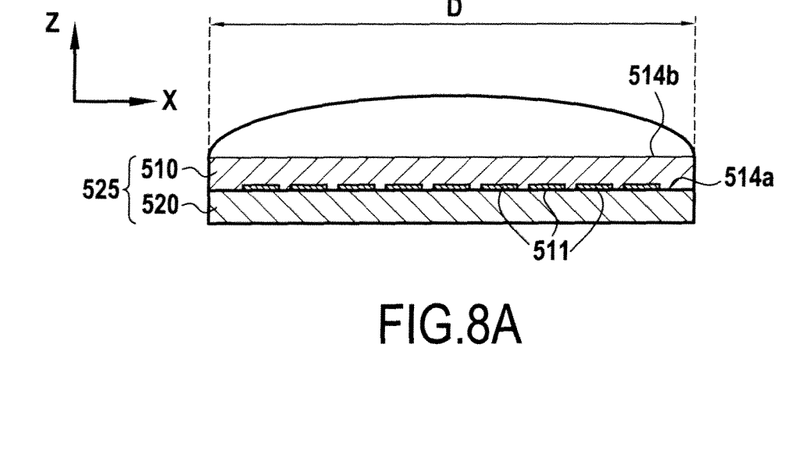
FIG. 8A represents a perspective half-section of a composite structure comprising a first wafer bonded to a second wafer.

To be more precise, there is considered here a composite structure 525 having a structure analogous to the structure 125 described hereinabove (FIG. 8A). The structure 525 thus comprises a first wafer 510 bonded by molecular adhesion to a second wafer 520. The first wafer 510 also comprises in this example microcomponents 511 on its bonding surface 514a, these microcomponents thus being buried at the level of the bonding interface.

Figure 8B:
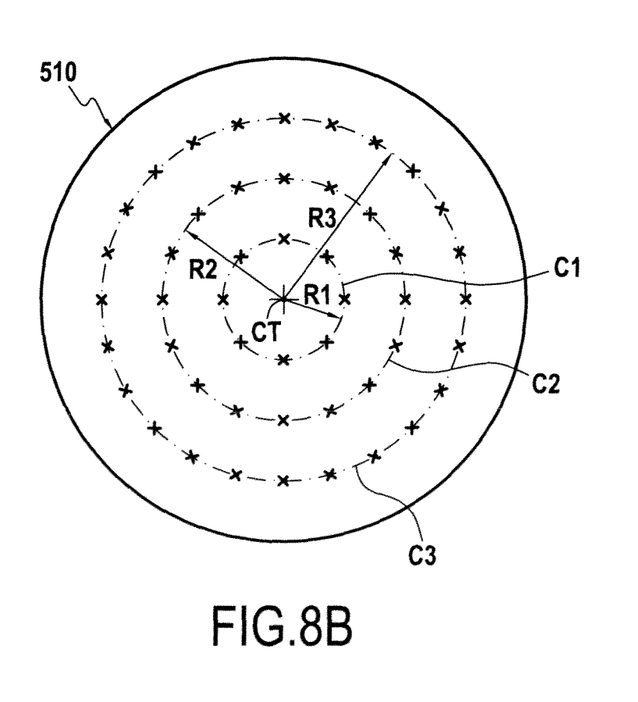
FIG. 8B represents the structure from FIG. 8A as seen from above.

In the logging step E1, the measurement points are disposed along at least one circle the centre of which coincides with the centre CT of the first wafer 510 (FIG. 8B). In the example described here, logging is carried out along three concentric circles denoted C1, C2 and C3, these circles having a radius R1, R2 and R3, respectively (these radii being less than that of the wafer 510).

It will be understood, however, that there may be any number of circles along which the measurement points are logged. This number may notably be chosen as a function of the accuracy and/or the reliability of the evaluation then to be carried out in the step E4. The number of circles and their respective radii are preferably chosen to distribute the measurement points uniformly over the surface of the wafer, so as to obtain data representative of the heterogeneous deformations over the whole of the wafer 510. Alternatively, it is possible to log measurement points along at least one circular arc the centre of curvature whereof coincides with the centre CT. It is equally possible to log measurement points along at least one spiral centred on CT.

At least one surface profile of the first wafer 510 is then determined in the step E2, each of these profiles passing through a plurality of measurement points of a corresponding log produced in the preceding step E1. In this example, three surface profiles P1, P2 and P3 are thus determined in the step E2, these corresponding to all of the measurement points logged along the circles C1, C2 and C3, respectively.

The spread of each surface profile obtained in the step E3 is then determined (step E4). This spread calculation may be implemented in different ways.

In a first variant, the minimum value Vmin(i) and the maximum value Vmax(i) of each of the surface profiles Pi (i=1, 2, 3) are determined. These values Vmin(i) and Vmax(i) correspond to the measurement points of the profile Pi locally representative of the lowest and highest level of the exposed surface of the wafer 510, respectively. There is then determined for each profile Pi the difference $\Delta i$ such that $\Delta i = Vmax(i) - Vmin(i)$.

On the basis of the values $\Delta i$, a third test is effected to evaluate the level of the non-homogeneous deformations present in the first wafer 510. A predetermined limit value $\Delta max$ is fixed, for example. The third test then consists in determining if $\Delta i \geq \Delta max$ (for i=1, 2 or 3). If so, the level of non-homogeneous deformations present in the wafer 510 is judged high. If not, the level of deformation is considered as low. The acceptability criterion $\Delta max$ associated with each value of the index i may be variable, notably increasing to the degree that the diameter of the circles C1 to C3 increases. For example, for circles with diameters of 65 mm and 145 mm, the values of $\Delta max$ could be equal to approximately 5 microns and 15 microns, respectively.

A variant of the third test consists firstly in summing the differences $\Delta i$ and then in dividing this result by what is commonly called the warp of the structure, defined by the difference between the maximum overall height of the surface on which logging is conducted and its minimum overall height. For a structure uniformly curved as a paraboloid of revolution, for example, the warp is equal to the bow of the structure. The second stage of this variant of the third test consists in determining if the coefficient between the sum of the $\Delta i$ and the warp is less than a predetermined value, for example of the order of 0.7. If so, the level of heterogeneous deformations is considered low. If not, the level of deformations is considered as high.

In a second variant, there is determined the standard deviation $\sigma i$ for each surface profile Pi. A fourth test is then carried out which consists in determining if $\sigma i$ is greater than or equal to a predetermined maximum standard deviation (for i=1, 2 or 3). If so, the wafer 510 is considered as having a high level of heterogeneous deformations. If not, the deformation level is considered low.

The variants described above are merely nonlimiting embodiments of the invention and the person skilled in the art will understand that other alternatives may be envisaged for determining the spread of a surface profile that do not depart from the scope of the invention.

The processing step E3 and the evaluation step E4 of the method of the invention may be implemented, for example, by a computer, a calculator or any other equipment capable of calculating a second derivative or a spread from measurement points of a surface profile and effecting a test relating to a second derivative or respectively a spread, such as one of the tests described above, for example.

The present invention further concerns a method (steps E1 to E5) of composite structures comprising a first wafer bonded by molecular adhesion to a second wafer.

The main steps of the selection method of one particular embodiment are shown in FIG. 3.

A level of heterogeneous deformations in a first wafer is first evaluated by successively effecting the steps E1, E2, E3 and E4 of the evaluation method of the invention on the composite structure.

During a selection step E5, there are then selected one or more composite structures identified in the step E4 as having a low level of non-homogenous deformations.

For example, it is possible to carry out the first and second tests or the third and fourth tests as described above. The composite structure or structures is or are then selected if the result of the tests effected is negative.

It is also possible to carry out only one of these tests. In this special case, the composite structure or structures is or are selected if the test carried out is negative.

However, the selection method of the invention is not limited to the two examples of tests described above. Other selection criteria bearing on the second derivative of a surface profile may be used, individually or in combination.

The logging of measurement points in the step E1 of the evaluation method may furthermore be carried out according to different lines on the exposed surface of the first wafer.

"Star" logging, i.e. logging on a plurality of diameters of the first wafer, may in, particular be envisaged. This technique enables a good representation to be obtained of the levels of heterogeneous deformations in a first wafer with a limited number of logs produced.

In one particular example, there is produced in the step E1 a plurality of logs of measurement points, logging being carried out along first parallel lines spaced from each other. It is furthermore possible to produce additional logs along second parallel lines spaced from each other and that may be perpendicular to the first lines, for example. Thus logging is carried out in accordance with a grid, which grid may be on the whole or part of the exposed surface of the first wafer considered.

Furthermore, if the first test described above is carried out, for example, of interest are only the changes of sign of the second derivative on the macroscopic scale. It is possible in practise that the exposed surface of the first wafer has infinitely small variations in level that are reflected in very localized changes of sign of the second derivative of the corresponding surface profile or profiles. These infinitesimally small variations may originate, for example, in very slight variations of thickness of the first wafer. This type of variation does not give usable information as to the level of heterogeneous deformations in the first wafer of a composite structure.

To avoid having to take into account negligible surface defects, it is possible to carry out logging in the step E1 so that the measurement points are measured according to a measurement step.

This measurement step could be chosen as a function of the situation concerned. It will preferably be chosen as a function of a dimension of a pattern of the first wafer.

Here "pattern" means a geometrical arrangement disposed, or intended to be disposed, on the exposed surface of a first wafer, this geometrical arrangement repeating several times over the surface of that wafer. A pattern may for example correspond to a cell of one or more microcomponents disposed at several locations on the exposed surface of the first wafer concerned.

For example, the measurement step may substantially correspond to half of one dimension of a pattern of the first wafer.

It will also be noted that the number of logs produced during the step E1 of the evaluation method could depend on various parameters such as, for example, the constraints of the fabrication process in terms of cost, time allotted to the tests for each batch of wafers, required level of reliability, etc.

Moreover, a give level of heterogeneous deformations may be acceptable for a given microcomponent technology (because it represents a relatively slight constraint in terms of positioning photolithography masks) and unacceptable for another technology. Consequently, the following parameters could be chosen depending on the situation concerned:
the choice of the number of logs to be produced,
the line of each log(length, direction),
the number of measurement points per log,
the measurement step used,
the method or methods of exploiting the second derivatives obtained in the step E2, and
the criterion or criteria for selection of the composite structures.

It will be noted here that numerous mechanisms may be the source of misalignments (or overlays) in a first wafer bonded by molecular adhesion to a second wafer.

When a first wafer is bonded by molecular adhesion to a second wafer, the heterogeneous deformations generated in the first wafer may notably result from combination of deformations originally present in the first and second wafers before bonding. The method of the invention can thus enable pertinent information to be obtained on the deformations of the two wafers before they are assembled by molecular adhesion (degree of concavity, flatness defects, etc.).

The present invention can also reveal, for example, the presence of foreign bodies such as a particle between the support S and the wafer directly in contact therewith. These elements may be the source of heterogeneous deformations in the first wafer and thus of misalignments.

The invention can equally highlight problems of calibration of the bonding machine (notably at the level of the application of the contact force by the applicator tool).

Moreover, as indicated above, once the composite structure has been formed by molecular adhesion, the first wafer generally undergoes thinning. Now, after thinning, the evaluation of the heterogeneous deformations by the method of the invention is no longer representative. It is therefore preferable to carry out the step E1 of the method of the invention before thinning the first wafer.

What is claimed is:

1. A method for evaluating inhomogeneous deformations in a plurality of multilayer structures, each multilayer structure comprising a first wafer bonded by molecular adhesion to a second wafer, which method comprises:
making at least one reading of a plurality of measurement points along a predefined direction and over a predefined length of each first wafer and producing a curve representative of a surface profile of each first wafer using the plurality of measurement points;
computing a second derivative from the curve representative of the surface profile of each first wafer;
evaluating a level of inhomogeneous deformations in each first wafer as a function of the second derivative, wherein evaluating the level of inhomogeneous deformations in each first wafer comprises at least one test of determining whether the second derivative presents at least one sign change; and
physically separating, based on the evaluating, the plurality of multilayer structures into a first group having an acceptable level of inhomogeneous deformations and a second group having an unacceptable level of inhomogeneous deformations,
wherein, for each multilayer structure, the making at least one reading of a plurality of measurement points comprises emitting, by a probe, an acoustic wave toward the multilayer structure such that the acoustic wave propagates in the first wafer and the second wafer and generates a plurality of echoes,
wherein, for each multilayer structure, the producing the curve comprises determining the curve based on at least one of the plurality of echoes, and
wherein the plurality of echoes includes a first echo generated at a rear surface of the second wafer, a second echo generated at a buried surface of the first wafer, and a third echo generated at an exposed surface of the first wafer.

2. The method according to claim 1, wherein the measurement points of each reading are measured along a diameter of each first wafer.

3. The method according to claim 1, wherein a plurality of readings of measurement points are made, with the readings being spaced from one another and made along the same direction.

4. The method according to claim 1, wherein the measurement points of each reading are measured according to a measurement pitch, with the measurement pitch being determined according to a dimension of at least one pattern of each first wafer.

5. The method according to claim 4, wherein the measurement pitch substantially corresponds to half of a dimension of a pattern of each first wafer.

6. The method according to claim 1, wherein the at least one reading of a plurality of measurement points is made by acoustic microscopy.

7. The method according to claim 1, wherein the at least one test comprises determining whether the second derivative presents at least one absolute value higher than a predefined value, and wherein physically separating the plurality of multilayer structures into the first group comprises selecting at least one multilayer structure when the result of the at least one test indicates the second derivative does not present the at least one sign change or the second derivative does not present the at least one absolute value higher than the predefined value.

8. The method according to claim 1, wherein the at least one test comprises determining whether the second derivative presents at least one absolute value higher than a predefined value, and wherein physically separating the plurality of multilayer structures into the second group comprises selecting at least one multilayer structure when the result of the at least one test indicates the second derivative presents the at least one sign change or the second derivative presents the at least one absolute value higher than the predefined value.

9. The method according to claim 1, wherein the surface profile of each first wafer includes multiple surface profiles, and wherein the at least one test comprises:
   determining a difference between minimum and maximum values of the multiple surface profiles; and
   determining whether the difference is greater than a variable limit value.

10. The method according to claim 1, wherein the surface profile of each first wafer includes multiple surface profiles, and wherein the at least one test comprises:
    determining differences between minimum and maximum values of the multiple surface profiles;
    summing the differences;
    calculating a coefficient by dividing the summed differences by a warp value; and
    determining if the coefficient exceeds a predetermined value, wherein the warp value is a difference between a maximum overall height of the multilayer structure and a minimum overall height of the multilayer structure.

11. The method according to claim 1, wherein the surface profile for each first wafer includes multiple surface profiles, and wherein the at least one test comprises:
    determining a standard deviation for the multiple surface profiles; and
    determining whether the standard deviation is greater than or equal to a predetermined maximum standard deviation.

12. The method according to claim 1,
    wherein the buried surface is between the rear surface of the second wafer and the exposed surface of the first wafer, and
    wherein the determining the curve includes at least one of:
       determining a distance between the probe and the exposed surface of the first wafer based on the third echo; and
       determining a thickness of the first wafer based on a time shift between receiving the second echo and the third echo.

13. A device for evaluating inhomogeneous deformations in a plurality of multilayer structures, each multilayer structure comprising a first wafer bonded by molecular adhesion to a second wafer, the device comprising:
    measurement means for making at least one reading of a plurality of measurement points along a predefined direction and over a predefined length of each first wafer and for producing a curve representative of a surface profile of each first wafer using the plurality of measurement points;
    computation means for computing a second derivative from the curve representative of the surface profile of each first wafer;
    evaluation means for evaluating a level of inhomogeneous deformations in each first wafer as a function of the second derivative, wherein the evaluation means is configured to perform at least one test comprising a determination of whether the second derivative presents at least one sign change; and
    sorting means for sorting the plurality of multilayer structures into a first group and a second group based on the evaluating,
    wherein, for each multilayer structure, the making at least one reading of a plurality of measurement points comprises emitting, by a probe, an acoustic wave toward the multilayer structure such that the acoustic wave propagates in the first wafer and the second wafer and generates a plurality of echoes,
    wherein, for each multilayer structure, the producing the curve comprises determining the curve based on at least one of the plurality of echoes, and
    wherein the plurality of echoes includes a first echo generated at a rear surface of the second wafer, a second echo generated at a buried surface of the first wafer, and a third echo generated at an exposed surface of the first wafer.

14. The device according to claim 13, wherein the measurement points of each reading are measured along a diameter of each first wafer.

15. The device according to claim 13, wherein the measurement means is configured to make a plurality of readings of measurement points, with the readings being spaced from one another and made along the same direction.

16. The device according to claim 13, wherein the measurement means is configured so that the measurement points of each reading are measured according to a measurement pitch, with the measurement pitch being determined according to a dimension of at least one pattern of each first wafer.

17. The device according to claim 16, wherein the measurement pitch substantially corresponds to half of a dimension of a pattern of each first wafer.

18. The device according to claim 13, wherein the measurement means comprises an acoustic microscope.

19. A device for evaluating inhomogeneous deformations in a plurality of multilayer structures, each multilayer structure comprising a first wafer bonded by molecular adhesion to a second wafer, the device comprising:
    an acoustic probe that emits, for each multilayer structure, an acoustic wave toward the multilayer structure such that the acoustic wave propagates in the first wafer and the second wafer and generates a plurality of echoes; and
    a processor coupled to a memory including instructions to cause the processor to:
       make at least one reading of a plurality of measurement points along a predefined direction and over a predefined length of each first and produce a curve representative of a surface profile of each first wafer using the plurality of measurement points;
       compute a second derivative from the curve representative of the surface profile of each first wafer;
       evaluate a level of inhomogeneous deformations in each first wafer as a function of the second derivative by performing at least one test comprising a determination of whether the second derivative presents at least one sign change; and
       sort the plurality of multilayer structures into a first group and a second group based on results of the at least one test,
    wherein, for each multilayer structure, the processor produces the curve by determining the curve based on at least one of the plurality of echoes, and wherein the plurality of echoes includes a first echo generated at a rear surface of the second wafer, a second echo generated at a buried surface of the first wafer, and a third echo generated at an exposed surface of the first wafer.

* * * * *